US00PP37764P2

(12) United States Plant Patent
Vandenberg

(10) Patent No.: US PP37,764 P2
(45) Date of Patent: Oct. 13, 2026

(54) ***HIBISCUS* PLANT NAMED 'Hot Pink Wind'**

(50) Latin Name: *Hibiscus rosa-sinensis*
Varietal Denomination: Hot Pink Wind

(71) Applicant: Cornelis P. Vandenberg, Fort Myers, FL (US)

(72) Inventor: Cornelis P. Vandenberg, Fort Myers, FL (US)

(73) Assignee: ARIS HORTICULTURE, INC., Barberton, OH (US)

( * ) Notice: Subject to any disclaimer, the term of this patent is extended or adjusted under 35 U.S.C. 154(b) by 0 days.

(21) Appl. No.: 19/544,987

(22) Filed: Feb. 19, 2026

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257

CPC . A01H 5/02; A01H 5/00; A01H 6/608; A01H 6/60

See application file for complete search history.

(56) References Cited

U.S. PATENT DOCUMENTS

PP25,236 P2 * 1/2015 Graff ..... A01H 5/02 Plt./257
PP35,220 P2 * 6/2023 Vandenberg ..... Plt./257

* cited by examiner

*Primary Examiner* — June Hwu
(74) *Attorney, Agent, or Firm* — C. Anne Whealy

(57) ABSTRACT

A new and distinct cultivar of *Hibiscus* plant named 'Hot Pink Wind', characterized by its upright to outwardly spreading and uniformly mounded plant habit appropriate for container production; freely branching habit, dense and bushy appearance; glossy dark green-colored leaves; uniform, freely and early flowering habit; and large bright purplish red-colored flowers with small dark red-colored throats.

2 Drawing Sheets

Figure 1:
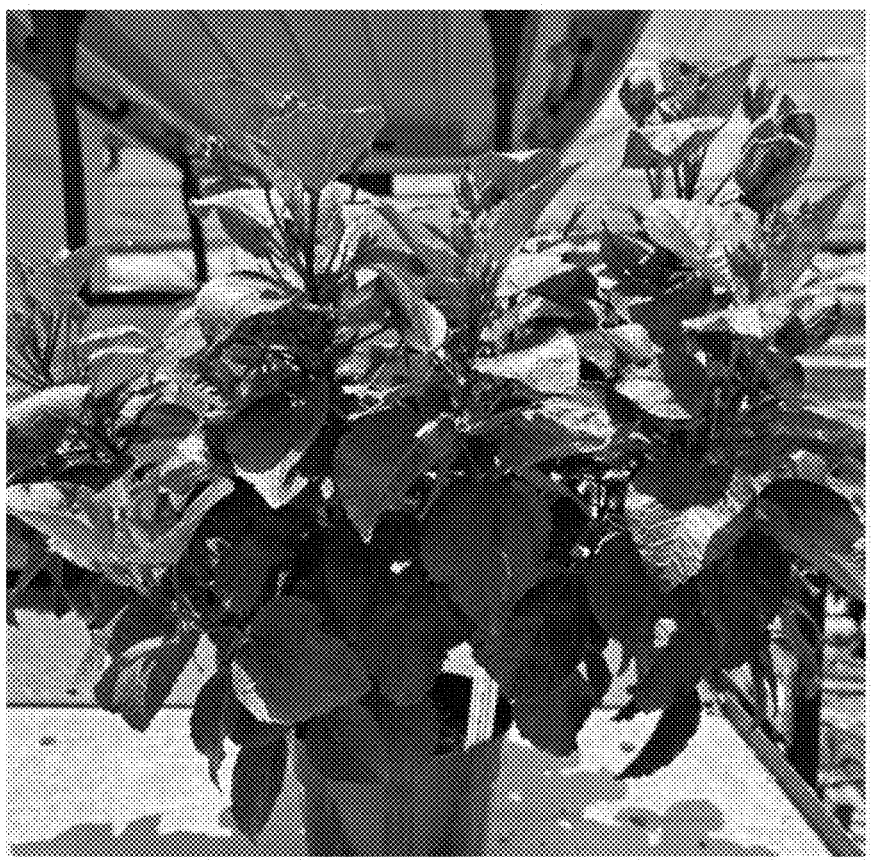

Botanical designation: *Hibiscus rosa-sinensis.*
Cultivar denomination: 'HOT PINK WIND'.

BACKGROUND OF THE INVENTION

The present invention relates to a new and distinct *Hibiscus* plant, botanically known as *Hibiscus rosa-sinensis* and hereinafter referred to by the name 'Hot Pink Wind'.

The new *Hibiscus* plant is a product of a planned breeding program conducted by the Inventor in Alva, Florida. The objective of the breeding program is to create new freely-branching *Hibiscus* plants with uniform plant habit appropriate for container production, early and freely flowering habit, and large attractive flowers.

The new *Hibiscus* plant originated from a cross-pollination made by the Inventor in Alva, Florida in 2022 of *Hibiscus rosa-sinensis* 'Cayman Wind', disclosed in U.S. Plant Pat. No. 23,760, as the female, or seed, parent with *Hibiscus rosa-sinensis* 'Yellow Lava Wind', disclosed in U.S. Plant patent application Ser. No. 18/395,598 (abandoned), as the male, or pollen, parent. The new *Hibiscus* plant was discovered and selected by the Inventor as a single flowering plant within the progeny of the stated cross-pollination in a controlled greenhouse environment in Alva, Florida on Jan. 9, 2023.

Asexual reproduction of the new *Hibiscus* plant by vegetative terminal cuttings in a controlled greenhouse environment in Alva, Florida since April, 2023 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hot Pink Wind'. These characteristics in combination distinguish 'Hot Pink Wind' as a new and distinct *Hibiscus* plant:

1. Upright to outwardly spreading and uniformly mounded plant habit appropriate for container production.
2. Freely branching habit, dense and bushy appearance.
3. Glossy dark green-colored leaves.
4. Uniform, freely and early flowering habit.
5. Large bright purplish red-colored flowers with small dark red-colored throats.

Plants of the new *Hibiscus* can be compared to plants of the female parent, 'Cayman Wind'. Plants of the new *Hibiscus* differ primarily from plants of 'Cayman Wind' primarily in flower color as flowers of the new *Hibiscus* have smaller dark red-colored throats than flowers of plants of 'Cayman Wind'. In addition, plants of the new *Hibiscus* are more upright than and not as outwardly spreading as plants of 'Cayman Wind'.

Plants of the new *Hibiscus* can be compared to plants of the male parent, 'Yellow Lava Wind'. Plants of the new *Hibiscus* differ primarily from plants of 'Yellow Lava Wind' primarily in flower color as flowers of the new *Hibiscus* are bright purplish red in color whereas flowers of plants of 'Yellow Lava Wind' are golden yellow in color. In addition, flowers of plants of the new *Hibiscus* have smaller dark red-colored throats than flowers of plants of 'Yellow Lava Wind'.

Plants of the new *Hibiscus* can be compared to plants of the *Hibiscus rosa-sinensis* 'Pink Flamingo Wind', disclosed in U.S. Plant Pat. No. 35,220. In side-by-side comparisons plants of the new *Hibiscus* differ from plants of 'Pink Flamingo Wind' in the following characteristics:

1. Plants of the new *Hibiscus* have larger flowers than plants of 'Pink Flamingo Wind'.
2. Flowers of plants of the new *Hibiscus* are lighter in color than flowers of plants of 'Pink Flamingo Wind'.
3. Flowers of plants of the new *Hibiscus* have smaller dark red-colored throats than flowers of plants of 'Pink Flamingo Wind'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet (FIG. 1) is a side perspective view of a typical flowering plant of 'Hot Pink Wind' grown in a container.

Figure 2:
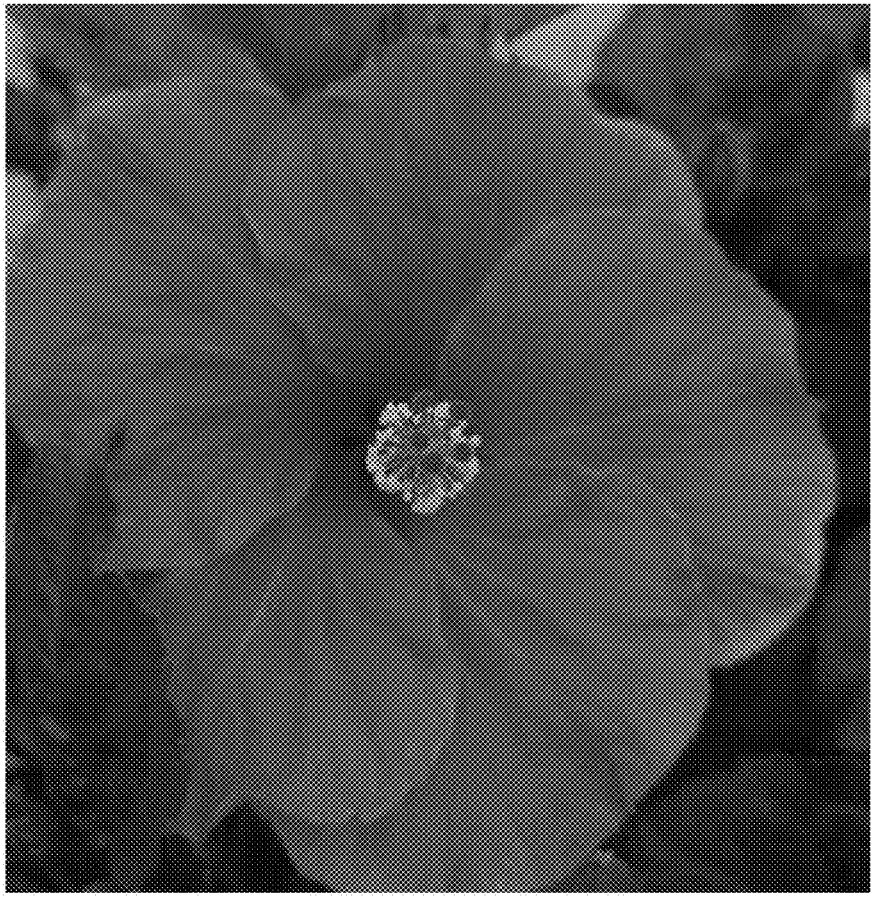

The photograph on the second sheet (FIG. 2) is a close-up view of a typical flower of 'Hot Pink Wind'.

DETAILED BOTANICAL DESCRIPTION

The aforementioned photographs and following observations, measurements and values describe plants grown during the autumn and winter in 15-cm containers in a polyethylene-covered greenhouse in Alva, Florida under cultural practices which closely approximate commercial *Hibiscus* production. During the production of the plants, day temperatures averaged 28° C., night temperatures averaged 18° C. and light levels ranged from 4,000 to 5,000 foot-candles. Plants were pinched two times and were seven months old when the photographs and the description were taken. In the description, color references are made to The Royal Horticultural Society Colour Chart, 2015 Edition, except where general terms of ordinary dictionary significance are used.

Botanical classification: *Hibiscus rosa-sinensis* 'Hot Pink Wind'.

Parentage:

*Female, or seed, parent.*—*Hibiscus rosa-sinensis* 'Cayman Wind', disclosed in U.S. Plant Pat. No. 23,760.

*Male or pollen parent.*—*Hibiscus rosa-sinensis* 'Yellow Lava Wind', disclosed in U.S. Plant patent application Ser. No. 18/395,598 (abandoned).

Propagation:

*Type.*—By vegetative terminal cuttings.

*Time to initiate roots, summer and winter.*—About four to five weeks.

*Time to produce a rooted young plant, summer and winter.*—About five to six weeks.

*Root description.*—Thick, fibrous; typically white to light brown in color, actual color of the roots is dependent on substrate composition, water quality, fertilizer, substrate temperature and physiological age of roots.

*Rooting habit.*—Moderate branching; moderately dense.

Plant description:

*Plant form and growth habit.*—Perennial, evergreen, semi-upright and uniformly mounded plant habit; moderately vigorous to vigorous growth habit.

*Branching habit.*—Freely branching habit with lateral branches potentially develop at every node; pinching enhances lateral branch development; dense and bushy appearance.

*Plant height.*—About 38 cm.

*Plant diameter* (*area of spread*).—About 49 cm.

Lateral branch description:

*Length.*—About 30.5 cm.

*Diameter.*—About 1.2 cm.

*Internode length.*—About 2 cm to 2.5 cm.

*Aspect.*—Upright to somewhat outwardly spreading.

*Texture and luster, immature.*—Smooth; glossy.

*Texture and luster, mature.*—Woody and rough; matte.

*Color, immature.*—Close to 146A variably overlain with close to 187A.

*Color, mature.*—Close to 199A to 199B.

Leaf description:

*Arrangement.*—Alternate, single; numerous; symmetrical.

*Length.*—About 9 cm.

*Width.*—About 7.5 cm to 7.75 cm.

*Shape.*—Broadly ovate.

*Apex.*—Acute.

*Base.*—Obtuse.

*Margin.*—Crenate.

*Texture and luster, upper surface.*—Smooth, glabrous; glossy.

*Texture and luster, lower surface.*—Smooth, glabrous; slightly glossy.

*Venation pattern.*—Pinnate; arcuate.

*Color.*—Developing leaves, upper surface: Close to 147A. Developing leaves, lower surface: Close to 146A. Fully expanded leaves, upper surface: Close to N189A. Fully expanded leaves, lower surface: Close to 147B.

*Petioles.*—Length: About 3.3 cm to 3.5 cm. Diameter: About 3 mm by 3.5 mm. Texture and luster, upper and lower surfaces: Smooth, glabrous; slightly glossy. Color, upper and lower surfaces: Close to 146A variably overlain with close to 187A.

Flower description:

*Flower arrangement and flowering habit.*—Rounded single flowers arranged at terminal leaf axils; uniform and freely flowering habit with about four to six flowers per terminal; flowers face mostly upright to outwardly.

*Natural flowering season.*—Plants of the new *Hibiscus* flower naturally during the spring and summer or during periods of warm weather; plants flower year-round in the greenhouse.

*Flower longevity.*—Depending on temperature and water status, flowers typically last about two to three days on the plant; flowers persistent.

*Flower diameter.*—About 12.5 cm.

*Flower length* (*height*).—About 8 cm.

*Flower buds, before showing petal color*.—Resistance to abscission during shipping: Plants of the new *Hibiscus* have been observed to resist flower bud drop during shipping. Length: About 2.75 cm. Diameter: About 1.3 cm. Shape: Ovoid. Texture and luster: Smooth, glabrous; semi-glossy. Color: Close to 147A.

*Petals*.—Arrangement: Corolla consists of a single whorl of five petals that are fused at base; petals imbricate. Length: About 7.5 cm. Width: About 6.5 cm. Shape: Spatulate, asymmetrical. Apex: Obtuse; undulate giving a frilled appearance. Base: Cuneate. Margin: Entire; proximally, not undulate and distally, undulate. Texture and luster, upper and lower surfaces: Smooth, glabrous; matte. Color: When opening and fully opened, upper surface: Close to N57A; towards the base, close to 53A. When opening and fully opened, lower surface: Close to 58B to 58C.

*Sepals*.—Appearance: Five sepals in a single whorl fused into a tubular star-shaped calyx. Length: About 5.5 cm. Width: About 1.2 cm. Shape: Lanceolate. Apex: Acuminate. Margin: Entire; not undulate. Texture and luster, upper surface: Smooth, glabrous; semi-glossy. Texture and luster, lower surface: Smooth, glabrous; matte. Color, upper and lower surfaces: Close to 144A.

*Epicalyx*.—Quantity and arrangement: About six in a single whorl fused at base. Length: About 2.4 cm. Width: About 6.5 mm. Shape: Linear. Apex: Acuminate. Margin: Entire; not undulate. Texture and luster, upper and lower surfaces: Smooth, glabrous; semi-glossy. Color, upper and lower surfaces: Close to 147A.

*Peduncles*.—Length: About 5.3 cm. Diameter: Proximally, about 3.5 mm; distally, about 5 mm. Aspect: Upright to slightly outwardly. Strength: Strong; flexible. Texture and luster: Smooth, glabrous; matte. Color: Close to 146A.

*Reproductive organs*.—Androecium: Stamen number: Numerous, about 45 to 55. Filament length: About 5 mm. Filament color: Close to 58B. Anther shape: Globular. Anther length: About 1.5 mm. Anther color: Close to 13A. Amount of pollen: Scarce. Pollen color: Close to 17A. Gynoecium: Pistil number: One per flower. Pistil length: About 8.5 cm. Style length: About 6.75 cm. Style texture and luster: Smooth, glabrous; semi- glossy. Style color: Proximally, close to 58B; distally, close to 58B to 58C. Stigma appearance: Five-parted, rounded. Stigma color: Close to 53A. Ovary color: Close to 154D.

*Seeds and fruits*.—To date, seed and fruit production has not been observed on plants of the new *Hibiscus*.

Garden performance: Plants of the new *Hibiscus* have been observed to tolerate wind, rain and temperatures ranging from about 2° C. to about 40° C.

Pathogen & pest resistance: To date, plants of the new *Hibiscus* grown under Florida production conditions have not been shown to be resistant to pathogen and pests common to *Hibiscus* plants.

It is claimed:

1. A new and distinct *Hibiscus* plant named 'Hot Pink Wind' as herein illustrated and described.

* * * * *